United States Patent [19]

Perkins et al.

[11] Patent Number: 5,300,702

[45] Date of Patent: Apr. 5, 1994

[54] RECOVERING VALUES FROM HEAVY ENDS IN BISPHENOL-A PRODUCTION

[75] Inventors: David A. Perkins; John E. Aiken, both of Monroeville, Pa.

[73] Assignee: Aristech Chemical Corporation, Pittsburgh, Pa.

[21] Appl. No.: 24,122

[22] Filed: Mar. 1, 1993

[51] Int. Cl.$^5$ .............................................. C07C 37/74
[52] U.S. Cl. .................................................. 568/724
[58] Field of Search ........................................ 568/724

[56] References Cited

U.S. PATENT DOCUMENTS

| | | | |
|---|---|---|---|
| 3,073,868 | 1/1963 | Prohl et al. | 568/724 |
| 4,209,646 | 6/1980 | Gac et al. | 568/724 |
| 4,447,655 | 5/1984 | Mendiralte | 568/724 |
| 4,825,010 | 4/1989 | Li | 568/724 |
| 4,954,661 | 9/1990 | Iimuro et al. | 568/727 |
| 5,105,026 | 4/1992 | Powell et al. | 568/724 |

OTHER PUBLICATIONS

Ketamura et al., Chem. Abst., vol. 110,#135897h(1989).
Nomura et al., Chem Abst., vol. 115,#50,495d(1991).
Hanaue et al., Chem. Abst., vol. 81,#78,458x(1994).

*Primary Examiner*—James H. Reamer
*Attorney, Agent, or Firm*—William L. Krayer

[57] ABSTRACT

In the production of bisphenol-A from the reaction of phenol and acetone, values are recovered from a "heavy ends" fraction by passing the fraction through a thin-film evaporator, making a light fraction which is fractionally distilled into three portions, two of which have recoverable proportions of bisphenol-A, and recovering bisphenol-A from at least one of them.

9 Claims, 4 Drawing Sheets

RECOVERING VALUES FROM HEAVY ENDS IN BISPHENOL-A PRODUCTION

TECHNICAL FIELD

This invention relates to the production of bisphenol-A and particularly to the recovery of values from the heavy ends in the production of bisphenol-A by the reaction of phenol and acetone.

BACKGROUND OF THE INVENTION

The manufacture of 2,2-bis(4-hydroxyphenyl) propane, or "bisphenol-A" ("BPA") by the reaction of phenol and acetone is well known and practiced commercially. See U.S. Pat. No. 3,242,219 and French Patents 1,179,377, 1,342,760, and 1,353,609.

Commonly produced in such manufacture is a waste stream which may comprise at least 50%, and up to about 90% (by weight) BPA. Because of the difficulty heretofore of recovering the BPA from the waste stream, it is generally burned along with the waste or otherwise disposed of at minimal value. In an HCl-catalyzed process, this stream typically is 3–4% of total plant production. Such waste streams may be produced, for example, in the crystallization processes described in "Industrial Crystallization for Ultrapure Products" by Charles G. Moyers, Jr., CEP May 1986, pp 42–46, and in U.S. Pat. No. 4,209,646.

We are not aware of a process similar to ours which is designed to recover values from a BPA waste stream such as we obtain in our plant, i.e. having from 50–90% para-para BPA (p,p-BPA), 5–35% ortho-para BPA (o,p-BPA) and 0–15% phenol, along with 5 to 30% other, higher molecular weight materials including about 3 to about 15% (based on the whole composition) of a reaction product of phenol and mesityl oxide, 2,2,4-trimethyl-4-hydroxyphenyl-chroman, which will be referred to herein as "codimer" (see the structural formula I below). Such a waste stream may be assumed to be present in the bottoms of column 13, described in the aforementioned U.S. Pat. No. 4,209,646, which is incorporated herein by reference in its entirety.

Additional compounds, included in "other" above, are 2,4,4-trimethyl-2-hydroxyphenyl-chroman (II), the isopropenyl dimer (III), "bisphenol-X", or trisphenol (IV), a spiro compound (V), a compound which may be referred to as "4 ring A" (VI) and one referred to as "14 ring B" (VII). Chroman is a particularly troublesome impurity because its boiling point is slightly lower than p,p-BPA, but higher than o,p-BPA. U.S. Pat. No. 4,954,661 teaches some steps similar to the present invention, but it is more complex and does not address the important issue of codimer removal.

p,p BPA o,p BPA

I

II

III

IV

V

VI

VII

SUMMARY OF THE INVENTION

We have invented a method of obtaining valuable products from a mixture comprising from about 50–90% p,p-BPA, about 5% to about 35% o,p-BPA, about 0% to about 15% phenol, about 3 to about 15% codimer and about 5% to about 30% other materials. Our method includes passing the mixture through a thin-film evaporator (preferably an agitated or wiped-film evaporator as described in pages 445–447, McCabe, W. L. and Smith, J. C., Unit Operations of Chemical Engr., 2nd Ed. McGraw Hill, 1967) to obtain a heavy fraction and a light fraction, totaling about 86–90% of the feed, fractionally distilling the light fraction to obtain (a) a fraction comprising primarily p,p-BPA, (b) a fraction comprising codimer, and (c) a fraction comprising o,p-BPA and phenol, and returning a portion of the column bottoms to the wiped-film evaporator for evaporation. Said p,p-BPA fraction (a) is recovered and recycled to a second-stage crystallization (such as in zone 10 in U.S. Pat. No. 4,209,646), and optionally said o,p-BPA phenol fraction (c) is passed back to a stirred tank reactor for isomerization of the o,p-BPA to the para-para isomer and condensation of the phenol with residual acetone.

We may choose to pass the fraction (c) through a separate isomerizing reactor (as described in U.S. Pat. No. 4,825,010) before returning it to the condensation reactor or crystallizer; alternatively, it may simply be returned to the original phenol/acetone reactor.

The codimer fraction (b) and the heavy fraction from the wiped-film evaporator may be burned as fuel or otherwise disposed of or employed such as an ingredient in plywood adhesives. A significant point of novelty in our process is that the codimer fraction (b) is removed by a sidedraw from the distillation column.

DETAILED DESCRIPTION OF THE INVENTION

The experimental program described below was used to develop the detailed process.

The proposed BPA heavy ends distillation process was simulated experimentally with a small continuous pilot unit. For simplicity, the experimental distillation unit was not equipped with a wiped-film evaporator (WFE) for a reboiler. Instead, the bottoms stream from the column was collected and later treated with a WFE in a separate setup. The experimental distillation apparatus is shown in block form in FIGS. 1 and 2.

Figure 1:
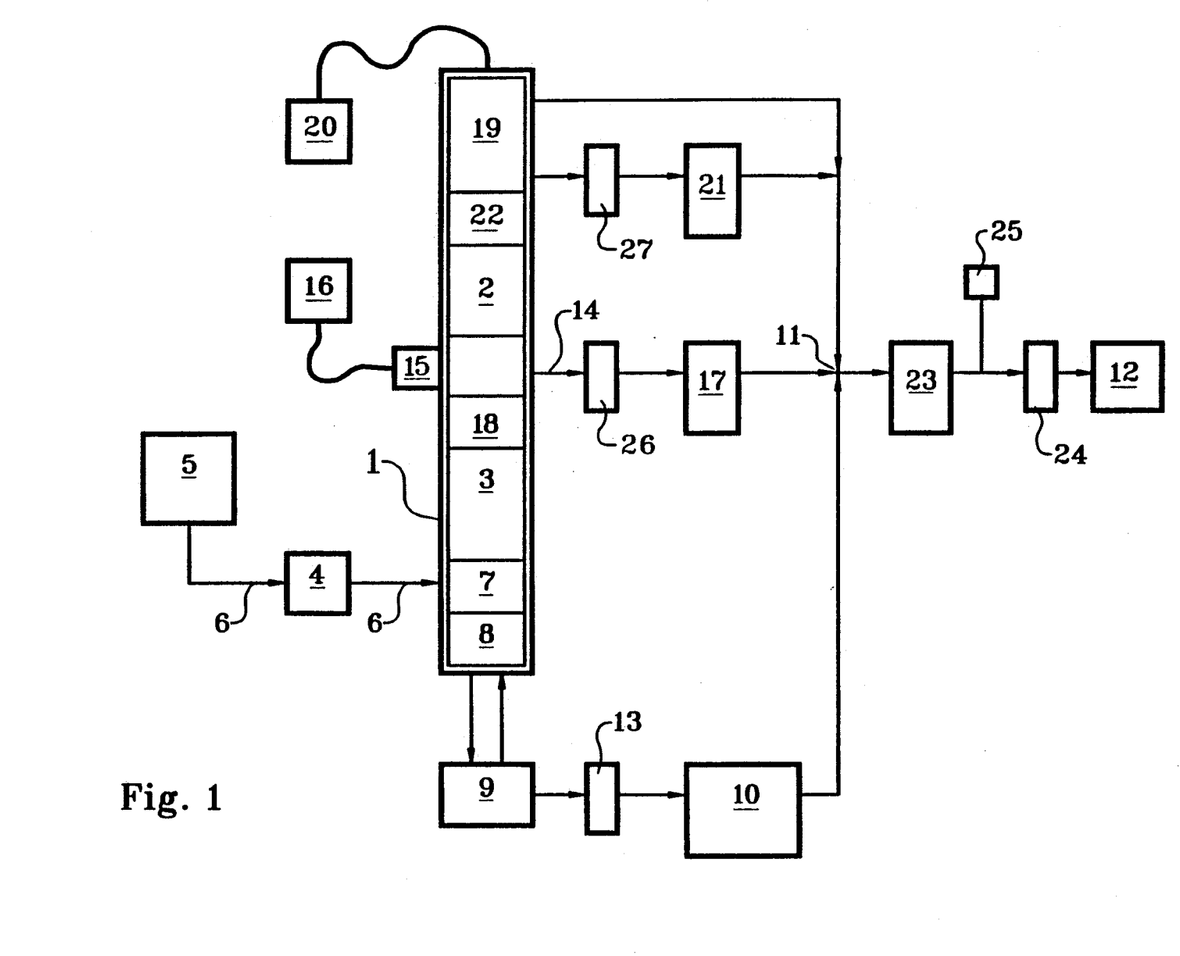
FIG. 1 is a flow diagram of the laboratory continuous distillation unit.

Referring to FIG. 1, the 1-inch-diameter distillation column 1 contains beds 2 and 3 of 0.16-inch 316 stainless steel Pro-Pak packing, each with a bed depth of 10 inches. Feed was pumped with an FMI lab pump 4 from a 3000-ml feed vessel 5 to the column 1 through a 0.25-inch-diameter 316 stainless steel feed line 6 which is heat-traced and insulated. The feed was introduced to the column at 7 below the lower packed bed 3 and above a section 8 containing two Oldershaw trays. Immediately below the Oldershaw section 8 was the reboiler 9, a 1000-ml round-bottomed flask which had been modified to minimize the reboiler residence time at about 30 minutes. The bottoms product flowed from the reboiler 9 to the bottoms receiver 10 which was connected to a vacuum at 11; vacuum was implemented by vacuum pump 12. Control of the bottoms rate was achieved by manipulation of a stopcock 13 to maintain a constant liquid level in the reboiler 9.

The codimer purge stream was removed by a sidedraw 14 from the column 1 between the two beds 2 and 3 of packing. A solenoid 15 was connected to a timer 16 to control the rate of liquid removal by alternately directing liquid flow down the column 1 and to the sidedraw 14. A graduated cylinder 17, which was connected to the vacuum at 11, was used to collect the codimer fraction and to measure the take-off rate. Located below the sidedraw 14 is a rate measurement section 18 with which the liquid rate in the column may be measured by determining the amount of time required to collect a known volume of liquid.

A condenser 19 was used that has two separate jackets for cooling water. Tempered water flows through a lower jacket (not shown) and cold tap water was used in an upper jacket. A reflux timer 20 regulated the flow rate of overhead product collected in a graduated cylinder 21. A reflux collector 22 was installed below the condenser 19 to return the reflux to the center of the top bed 2 of packing.

Vacuum was pulled on the top of the condenser 19 and the bottoms receiver 10, and graduated cylinders 17 and 21 with a vacuum pump 12. To prevent any water or organics from contaminating the vacuum pump 12, a dry ice trap 23 was located between the pump and the distillation system. A Cartesian diver 24 was used to control the pressure at approximately 5 Mm Hg, measured with a vacuum gauge 25 between the dry ice trap and the diver.

Thermocouples, controllers, heating tape and mantles, timers, and heat lamps were all wired to a common control panel (not shown). The heat input to the reboiler and feed line heat tracing were regulated by temperature controllers.

Experimental runs of up to 8 hours in length were made, with up to 6 hours of steady-state operation. To start up the unit, the feed vessel 5 was warmed up. When the temperatures of the feed vessel 5 and feed line 6 reached 130°–140° C., heavy ends preheated to 1500° C. were poured into the feed vessel 5. The feed pump 4 was switched on when the reboiler 9 temperature reached 1500° C. See Table 1 for the composition of the feed.

The variacs for the heating tape and mantle for the column upper section 2 were then turned on and the cooling water flow through condenser 19 was begun. Bottoms receiver 10 and graduated cylinders 17 and 21 were also warmed up. When vapors began condensing overhead, timers 16 and 20 were turned on to begin collection of overhead and sidedraw samples. Bottoms removal was begun when the liquid in the reboiler 9 reached the 210 ml level.

Thermocouple readings, variac settings, and the system pressure were monitored and the data were recorded every hour. The feed and overhead and sidedraw product levels were recorded every 10–15 minutes to check the feed and product rates. The liquid rate in rate measurement section 18 of column 1 was also measured periodically. The level of reboiler 9 was checked frequently and the bottoms removal rate was controlled by adjusting stopcock 13 in the line. Graduated cylinders 17 and 21 were changed periodically when the cylinder 21 became full. Heavy ends at 1500° C. were added to the feed vessel 5 as needed.

When all the feed in feed vessel 5 was gone, the unit was shut down by first closing the stopcocks 13, 26 and 27 at the same time to terminate collection of the steady-state fractions. Finally, the products were weighed, sampled, and transferred to labeled jars.

Figure 2:
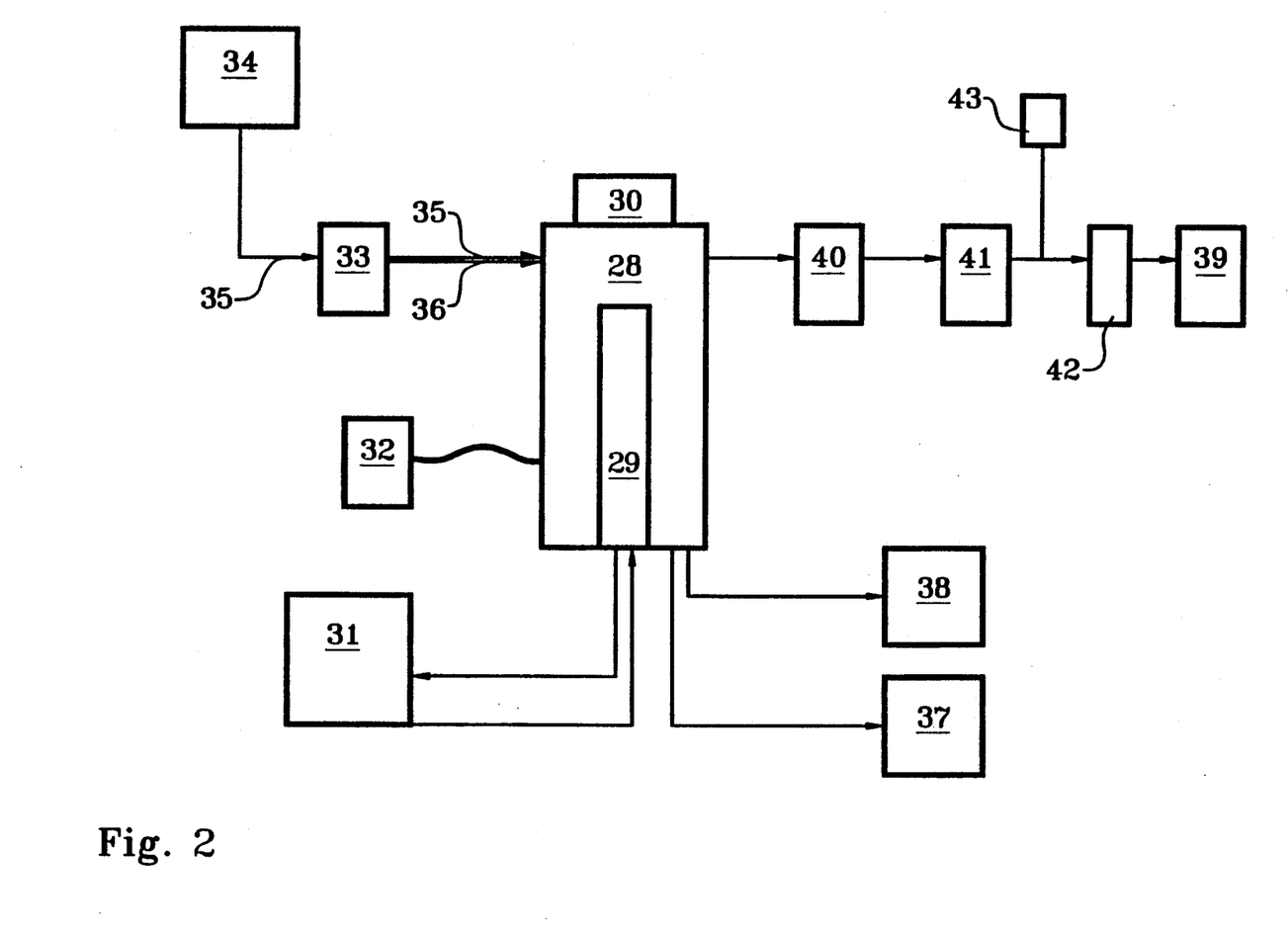
FIG. 2 is a flow diagram of the laboratory continuous WFE unit.

In FIG. 2, a flow diagram of the continuous WFE unit is shown. A 2-inch-diameter lab-scale wiped-film evaporator 28 manufactured by Pope Scientific was utilized in the experiments. The WFE 28 was equipped with an internal condenser 29 and a 1/15th hp motor 30 for rotation of the wiper blades. A hot oil bath 31 supplied 295° F. hot oil as the cooling medium to the internal condenser. A WFE jacket temperature of 518° F. was maintained by a temperature controller 32.

Bottoms material from the continuous distillation column unit was pumped with an FMI lab pump 33 from a 1000-ml feed vessel 34 through a 0.25-inch-diameter 316 stainless steel feed line 35 into the WFE 28. The feed line was wrapped with electrical heat tracing 36. The distillate was collected in a 500-ml round-bottomed receiver 37, and WFE bottoms material was collected in a separate 500-ml round-bottomed receiver 38.

Vacuum was pulled on the WFE 28 by a vacuum pump 39. To prevent any organics from contaminating the vacuum pump 39, a wet ice trap 40 and a dry ice trap 41 were located between the WFE 28 and the vacuum pump 39. The pressure in the system was maintained at 8 Mm Hg using a Cartesian diver 42 pressure controller. A pressure gauge 43 was located between the dry ice trap 41 and the pressure controller 42.

Before introducing feed to the WFE 28, the feed vessel 34, feed line heat tracing 36, and WFE jacket were preheated. When the temperatures approached the desired values, the feed pump 33 was turned on. The wiper blades motor 30 was turned on and set at a wiper blade speed setting of 100%. The feed material was preheated to 320° F. in the feed line 35 by the electrical heat tracing 36. The temperature of the WFE jacket was maintained at 518° F. by temperature controller 32 in order to distill off approximately 90%% of the feed.

After the unit had reached steady state, the distillate receiver 37 was switched and a steady state distillate sample was collected. The distillate receiver 37 was then switched back to the first receiver when all of the feed material was gone. The various fractions were then weighed, sampled, and transferred to labeled jars. Samples of the feed (column bottoms), WFE distillate, and WFE bottoms were analyzed by gas chromatography; the results of which are given in Table 1.

This laboratory demonstration was intended to answer three important questions: (1) Can the system be operated free of any intractable operating problems? (2) Can approximately 50% or more of the codimer in the feed be removed with acceptable yield? and, (3) What effect does recycle of the recovered material have on BPA quality? Several experiments were performed with the laboratory distillation unit, and separate WFE runs were also made. Column overheads were recycled to the laboratory BPA reactors, and WFE distillate (analogous to the p,p-BPA fraction) was recycled to the lab batch crystallizer.

A summary of the results of the experimental program is provided in Table 1. The system was operated several times for up to six hours at steady state with no serious operating problems. After optimizing the reboiler controller settings, the unit's operation was remarkably steady. The findings of primary importance are that there was no effect upon recycle of the recovered material on reactor (epoxy-grade) or crystallizer (polycarbonate-grade) product, even at recycle rates 3–4 times the required rates. Analysis of the various column fractions by gas chromatography indicated that 35.1% of the codimer was removed by the liquid sidedraw. The sidedraw was determined to contain 18.4% codimer.

As stated above, a target value of 50% of the codimer is to be removed by the unit. A computer model of the laboratory system was made and showed that, given the configuration of the experimental unit and the operating conditions of our experiments, the above results satisfactorily demonstrated the efficacy of the design. Additional computer modeling showed that the commercial design (i.e., WFE used as column reboiler rather than operated separately) would remove 50% of the codimer by use of the liquid sidedraw.

TABLE 1

| Summary of Experimental Results | |
|---|---|
| Height of packing | two 10" beds |
| Reboiler temperature (°F.) | 509 |
| Column midpoint temperature (°F.) | 444 |
| Column overhead temperature (°F.) | 388 |
| Operating pressure (mm Hg)* | 6 |
| Overhead rate/feed rate | 16.5% |
| Sidedraw rate/feed rate | 11.4% |
| Column bottoms rate/feed rate | 72.1% |
| Liquid rate at column midpoint/feed rate | 73.8% |

| | | Stream Compositions (wt %) | | | | |
|---|---|---|---|---|---|---|
| Stream | Feed | Over-head | Column Bottoms | Sidedraw | WFE Dist. | WFE Bottoms |
| Phenol | 5.3 | 31.3 | 0 | 0.4 | 0 | 0 |
| p,p-BPA | 63.5 | 4.4 | 82.2 | 24.7 | 84.9 | 65.2 |
| o,p-BPA | 21.1 | 54.3 | 8.8 | 56.5 | 9.5 | 4.0 |
| Codimer | 5.2 | 9.5 | 2.5 | 18.4 | 2.7 | 1.0 |
| BPX | 4.9 | 0.5 | 6.6 | 0 | 2.9 | 29.8 |
| Totals g/min | 7.4 | 1.2 | 5.3 | 0.8 | | |

*measured downstream of dry ice trap 23. It is suspected that the column top pressure was a few millimeters higher.

The primary difference between the experimental unit and the design of the commercial process was that the experimental unit did not use a WFE as a reboiler. Instead, the column bottoms were collected and treated separately with a WFE to obtain the p,p-BPA fraction. The lab unit was run with a conservative reboiler residence time of 30 minutes. The commercial unit, with a thin film evaporator as a reboiler, would operate with a much lower residence time, a lower reboiler temperature, and minimal thermal cracking of BPA. The commercial unit would thus have an improved yield and less cracking products in the recycle material compared to the demonstration unit.

The use of lab scale Pro-Pak packing rather than a wire mesh structured packing constituted a minor difference. Another minor difference was the use of a 2-tray Oldershaw column section between the column feed point and the reboiler. This was done to strip the lower boiling components in the feed before they reached the reboiler. Past experience with this type of reboiler has shown that excessive amounts of light materials are lost to the bottoms because the reboiler performs as less than one theoretical stage.

In a pilot-plant trial with a 4.2 ft$^2$ Pfaudler WFE, it was demonstrated that 85 to 90%% of the feed material could be vaporized at a rate of about 38 lb/hr-ft$^2$. The distillate from this trial contained all the codimer in the feed and imparted unacceptable color to the product when recycled.

Figure 3:
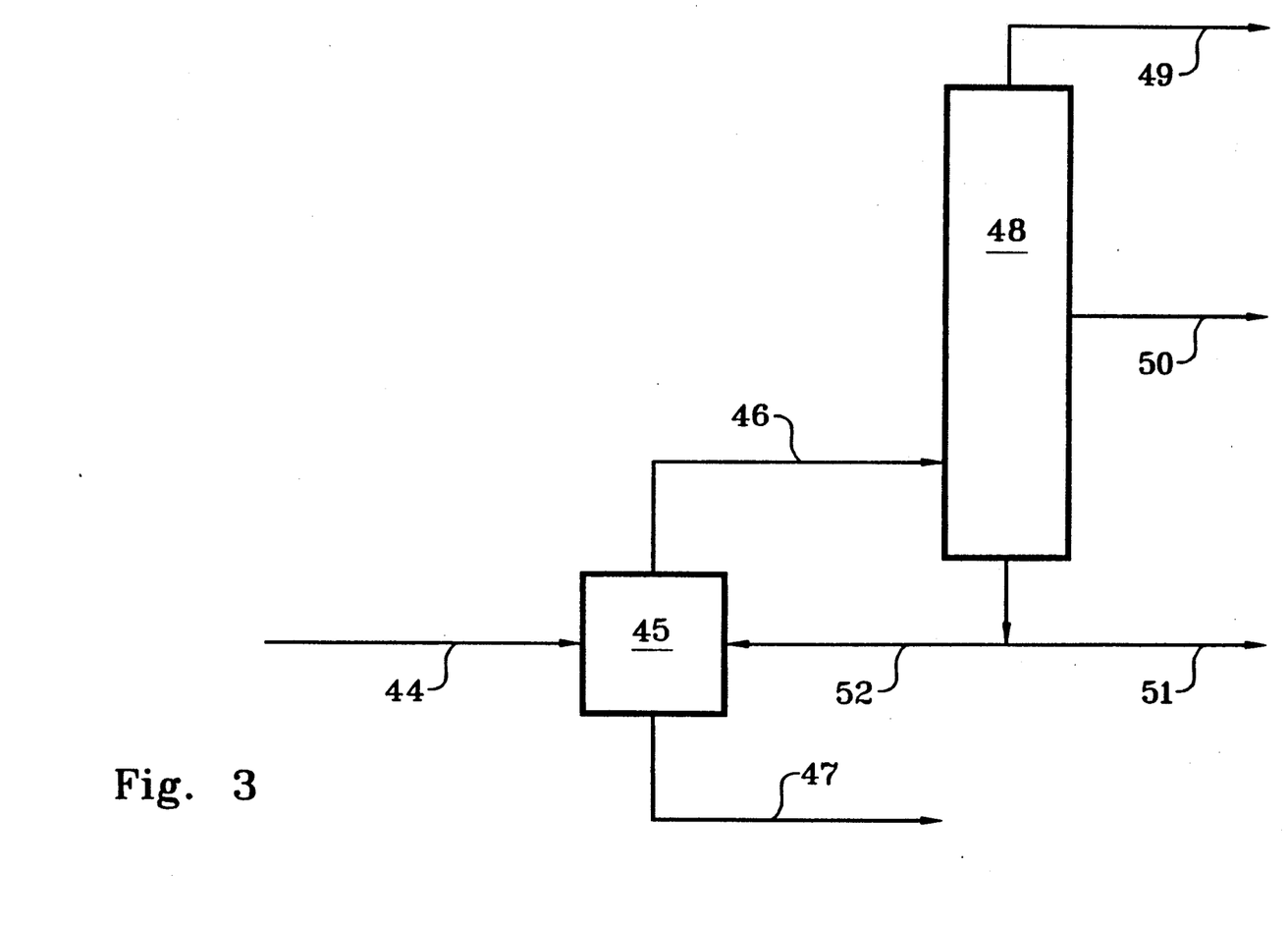
FIG. 3 shows a block flow diagram of our heavy ends distillation process.

Based on the experimental results, we use the following conditions and steps in our process, which is shown more or less diagrammatically in FIG. 3.

In FIG. 3, the "heavy ends" input stream 44 as defined above is entered into a wiped-film evaporator 45 to provide from about 30 to about 45 pounds per hour per square foot of heat transfer surface. As is known in the art, a wiped-film evaporator does not merely maintain a thin film on the evaporator surface by maintaining a fixed clearance, but agitates a film by remaining in direct contact with the product on the heated surface, i.e. by "trying" to contact the heat exchange surface directly. A wiped film is thus not only thinner than a simple "thin film" but implies a significant degree of agitation, a very thin film, and a very short residence time; in combination with a vacuum, the wiped-film evaporator is known for its ability to vaporize heat-sensitive materials before they decompose on the heated surface. Wiped-film evaporations may be compared in terms of pounds per hour of distillate treated per square foot of surface—however, even this will of course vary with the particular material treated. Any of the commercially available wiped-film evaporators will be suitable for our purposes; the volume limits of throughput are determined by the equipment itself but typically will not operate properly if a wiped film as described above is not maintained. A more complete description of a typical wiped-film evaporator which may be used in our invention may be found in Pfaudler's "Wiped-Film Evaporator" Sales Bulletin SB 39-100-1, pp 1-8, 1984, which is incorporated herein by reference. We do not intend to be restricted to any particular model or style of wiped-film evaporator, however.

Again referring to FIG. 3, the wiped-film evaporator divides the input stream 44 into a lights stream 46 and a heavies stream 47. The heavies stream 47 is removed for discarding or other uses not relevant here. The lights stream is forwarded to a distillation column 48 where it is divided into three streams, namely, the isomer/phenol stream 49, containing o,p-BPA and phenol, which may be returned to the original reaction, the codimer stream 50 which may be burned or otherwise utilized and the BPA-product stream 51 which is an excellent product of p,p-BPA suitable for a crystallization or other purification step. A portion of the column bottoms is returned to the WFE 45 by stream 52.

A detailed description of the commercial heavy ends treatment unit follows. A flow diagram of the process is given in FIG. 4. The computer model was used to generate the material balance (Table 2) and other design parameters. The feed composition was determined from analyses of plant samples and projected recycle streams to be approximately 3.4% phenol, 67.4% p,p-BPA, 17.2% o,p-BPA, 5.7% codimer, 5.1% BPX, and 1.0% water. This stream is typical of the waste streams obtained from the crystallization process for plants employing acid catalyst in the condensation reaction.

Figure 4:
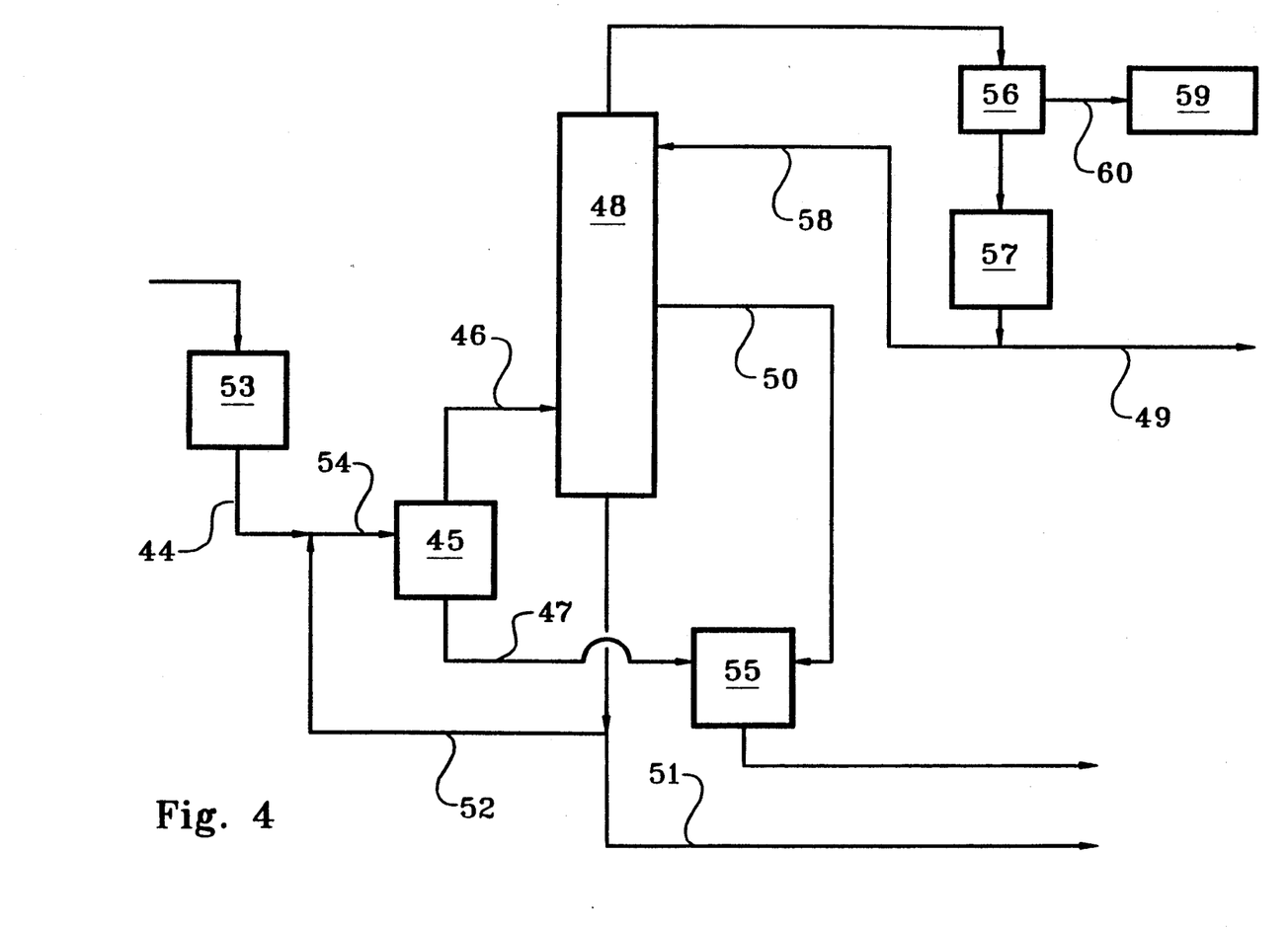
FIG. 4 is an integrated flow diagram of a heavy ends process of our invention.

A heavy ends feed drum 53 provides surge volume for the heavy ends material entering the process. The feed (stream 44) is pumped into a jacketed wiped-film evaporator 45 at a temperature of 329° F. A portion of the column bottoms (stream 52) is mixed with the heavy ends stream 44 before entering the WFE 45. The heating medium in the WFE is a typical heat transfer oil available commercially, which enters the WFE jacket at 600° F.

Approximately 90%% of the combined feed (stream 54) is vaporized in the WFE 45. The heavies material not vaporized in the WFE (stream 47) flows to the heavy ends waste drum 55. The vapor from the WFE 45 (stream 46) enters the bottom of the heavy ends distillation column 48. The heavy ends distillation column 48 contains two beds of corrosion-resistant structured packing. The top bed has a height of 10 ft and the bottom bed has a height of 7 ft. Together, the two beds provide about 20 theoretical stages of fractionation. The structured packing provides high efficiency and low pressure drop, minimizing the required temperature in the evaporator and thus the amount of thermal cracking of the BPA. The heavy ends column 48 is operated at an overhead pressure of 5 mmhg absolute, and the overall column pressure drop is about 5 mmHg.

A liquid sidedraw located between the two beds of packing is used to remove the codimer fraction 50 from the column 48. The codimer fraction 50 flows to the heavy ends waste drum 55, where in combination with the WFE bottoms stream, it becomes the ultimate waste product of this process. This stream may be useful as an ingredient in certain phenol/formaldehyde resins, or it may be used as a boiler fuel.

The p,p-BPA fraction 51, which contains over 90%% p,p-BPA, is drawn from the bottom of the column and pumped to the crystallization area for recovery of the p,p-BPA. The overhead vapors are cooled to 120° F. in the heavy ends column condenser 56. The condensed o,p-BPA and phenol flows to a reflux drum 57. Part of this stream is refluxed to the column above the upper bed of packing (stream 58). The remainder of this stream is the recovered o,p-BPA/phenol fraction 49, which is pumped to the reaction area for recovery of the phenol and isomerization of the ortho-para isomer.

Vapors are drawn from the distillation system by a vacuum system 59. The non-condensed stream 60 contains most of the water and a portion of the phenol from the heavy ends feed 44.

TABLE 2

| Component | Feed Stream No. 44 | | Condenser Effluent 60 | | Waste Stream 47 | | Codimer Purge 50 | | Btms Recycle 51 | | Ovhd Recycle 49 | |
|---|---|---|---|---|---|---|---|---|---|---|---|---|
| | lb/hr | wt % | lb/hr | wt % | lb/hr | wt % | lb/hr | wt % | lb/hr | wt % | lb/hr | wt % |
| Phenol | 45.8 | 3.4 | 14.7 | 44.4 | 0 | 0 | 0 | 0 | 0.1 | 0 | 31.0 | 19.0 |
| p,p-BPA | 910.1 | 67.4 | 0 | 0 | 64.8 | 46.3 | 39.6 | 30.5 | 805.7 | 91.0 | 0 | 0 |
| o,p-BPA | 231.9 | 17.2 | 0.6 | 1.7 | 5.7 | 4.1 | 43.7 | 33.6 | 57.0 | 6.4 | 124.8 | 76.7 |
| Codimer | 76.4 | 5.7 | 0 | 0 | 2.1 | 1.5 | 46.7 | 35.9 | 21.1 | 2.4 | 6.5 | 4.0 |
| BPX | 68.5 | 5.1 | 0 | 0 | 67.4 | 48.1 | 0 | 0 | 1.1 | 0.1 | 0 | 0 |
| Water | 13.5 | 1.0 | 13.0 | 39.3 | 0 | 0 | 0 | 0 | 0 | 0 | 0.5 | 0.3 |
| Air | 4.8 | 0.4 | 4.8 | 14.6 | 0 | 0 | 0 | 0 | 0 | 0 | 0 | 0 |
| Total | 1350.8 | | 33.0 | | 140.0 | | 130.0 | | 885.0 | | 162.8 | |
| Temp. °F. | 329 | | 120 | | 474.9 | | 413.9 | | 456.7 | | 120.0 | |

We claim:

1. Method of recovering values from a waste stream in the production of bisphenol-A by the reaction of phenol and acetone in a reaction zone, said waste stream having a composition comprising about 50–90% by weight p,p-bisphenol-A, about 5% to about 35%-o,p-bisphenol-A, about 0% to about 15% phenol, about 3% to about 15% 2,2,4-trimethyl-4-hydroxyphenyl-chroman and about 5% to about 30% other materials, comprising (a) introducing said waste stream into a thin-film evaporator to separate a heavy stream therefrom and recover at least about 70% of said waste stream in the form of a light stream, (b) introducing said light stream to a distillation tower to separate said light stream into (i) a fraction comprising at least about 70% p,p-BPA, (ii) a fraction comprising at least about 30% 2,2,4-trimethyl-4-hydroxyphenyl-chroman, and (iii) a fraction comprising phenol and at least about 40% o,P-BPA, and recovering the p,p-BPA values from stream (i).

2. Method of claim 1 wherein fraction (iii) is returned to said reaction zone for recovery of BPA values therein.

3. Method of claim 1 including introducing said stream (iii) into an isomerizer to convert o,p-BPA to p,p-BPA, and recovering the p,p-BPA values in fractions (i) and (iii).

4. Method of claim 1 wherein said thin-film evaporator is a wiped-film evaporator.

5. Method of claim 2 wherein said thin-film evaporator is a wiped-film evaporator.

6. Method of claim 3 wherein said thin-film evaporator is a wiped-film evaporator.

7. Method of claim 1 wherein said fraction (i) comprises at least about 80% BPA.

8. Method of claim 1 wherein said fraction (ii) comprises about 30% to about 60% 2,2,4-trimethyl-4-hydroxyphenyl-chroman.

9. Method of claim 1 wherein said fraction (iii) comprises about 60% to about 90% o,p-BPA.

* * * * *

UNITED STATES PATENT AND TRADEMARK OFFICE
CERTIFICATE OF CORRECTION

PATENT NO. : 5,300,702

DATED : April 5, 1994

INVENTOR(S) : Perkins et al

It is certified that error appears in the above-identified patent and that said Letters Patent is hereby corrected as shown below:

Column 1, line 53, change "14" to -- 4 --.

Column 4, line 59, change "15000" to -- 150° --;
line 62, change "15000" to -- 150° --.

Column 5, line 15, change "15000" to -- 150° --;
line 56, delete "90%%" and substitute -- 90% --.

Column 7, line 15, delete "90%%" and substitute -- 90% --.

Column 8, line 26, delete "90%%" and substitute -- 90% --;
line 54, delete "90%%" and substitute -- 90% --.

Column 9, line 22, claim 1, change "35%-o,p-" to -- 35% o,p-".

Signed and Sealed this

Sixteenth Day of August, 1994

Attest:

BRUCE LEHMAN

Attesting Officer

Commissioner of Patents and Trademarks